US011759345B2

(12) United States Patent
Di Pardo et al.

(10) Patent No.: US 11,759,345 B2
(45) Date of Patent: Sep. 19, 2023

(54) APPARATUS WEARABLE BY A SUBJECT FOR ASSISTING FORWARD RECLINING MOVEMENTS OF THE TORSO

(71) Applicant: C.R.F. Società Consortile per Azioni, Orbassano (IT)

(72) Inventors: Massimo Di Pardo, Orbassano (IT); Francesca Gallo, Orbassano (IT)

(73) Assignee: C.R.F. SOCIETÀ CONSORTILE PER AZIONI, Orbassano (IT)

( * ) Notice: Subject to any disclaimer, the term of this patent is extended or adjusted under 35 U.S.C. 154(b) by 217 days.

(21) Appl. No.: 17/118,852

(22) Filed: Dec. 11, 2020

(65) Prior Publication Data

US 2021/0282956 A1   Sep. 16, 2021

(30) Foreign Application Priority Data

Mar. 12, 2020   (EP) .................................... 20162846

(51) Int. Cl.
*A61F 5/02*   (2006.01)
*A61B 5/11*   (2006.01)
(Continued)

(52) U.S. Cl.
CPC ............ *A61F 5/028* (2013.01); *A61B 5/1116* (2013.01); *A61B 5/6812* (2013.01);
(Continued)

(58) Field of Classification Search
CPC .............. A61F 5/028; A61F 2005/0139; A61F 2005/0155; A61F 2005/0179;
(Continued)

(56) References Cited

U.S. PATENT DOCUMENTS 7,364,557 B2 * 4/2008 Yumikino ............. A61F 5/0125
602/19
2010/0036302 A1 * 2/2010 Shimada .................. A61H 3/00
602/23
(Continued)

FOREIGN PATENT DOCUMENTS

EP   3046517 B1   3/2015
FR   2885194 A1 * 11/2006 ........ F16F 15/13453
(Continued)

OTHER PUBLICATIONS

Translation of FR-2885194-A1 (Year: 2006).*
European Search Report dated Sep. 28, 2020.

*Primary Examiner* — Rachael E Bredefeld
*Assistant Examiner* — Seth R. Brown
(74) *Attorney, Agent, or Firm* — Heslin Rothenberg Farley & Mesiti P.C.; Victor A. Cardona, Esq.

(57) ABSTRACT

An assistance apparatus wearable by a subject for an assistance in forward reclining movements of the torso includes an upper structure for the engagement of the subject's torso and a lower structure for the engagement of the subject's legs, pivotally connected to each other around an axis, at least one elastic device operatively interposed between the upper structure and the lower structure and at least one electric motor operatively arranged in series with the elastic device, between the upper structure and the lower structure, and actionable for dynamically controlling the extent of deformation of the elastic device.

11 Claims, 8 Drawing Sheets

Figure 2:
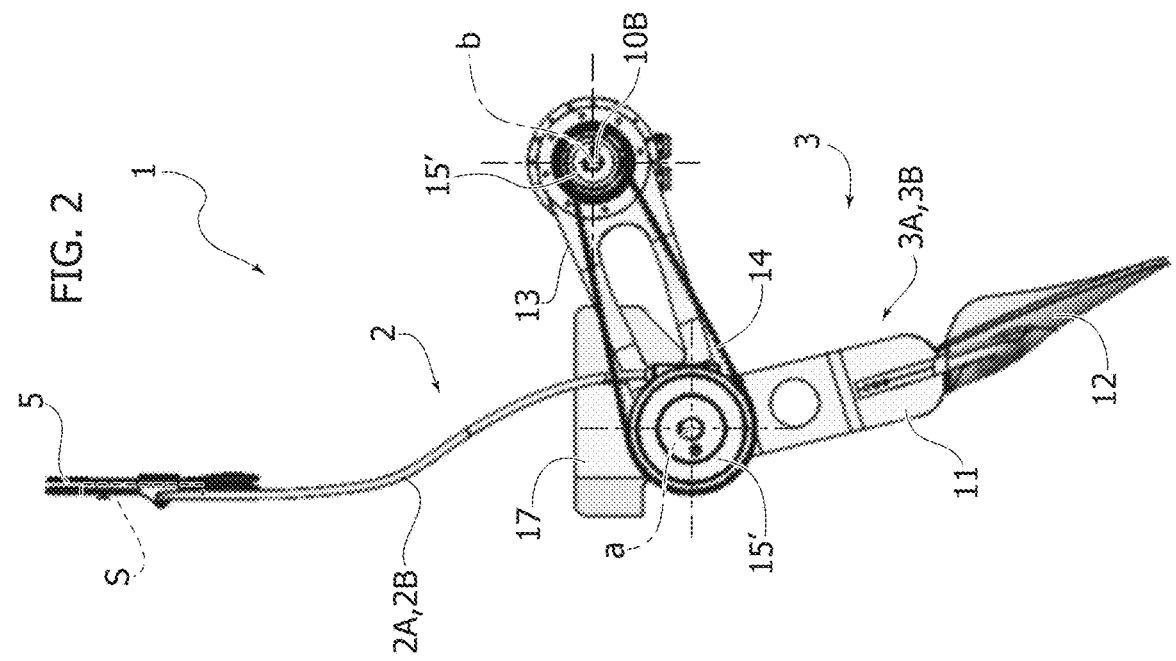

(51) Int. Cl.
*A61B 5/00* (2006.01)
*A61F 5/01* (2006.01)

(52) U.S. Cl.
CPC .... *A61B 5/6823* (2013.01); *A61F 2005/0139* (2013.01); *A61F 2005/0155* (2013.01); *A61F 2005/0179* (2013.01)

(58) Field of Classification Search
CPC ... A61B 5/1116; A61B 5/6812; A61B 5/6823; A61H 2201/1602; A61H 2201/1623; A61H 2201/1628; A61H 2201/164; A61H 2201/165; A61H 3/00; A61H 2003/007; A61H 1/023702
See application file for complete search history.

(56) References Cited

U.S. PATENT DOCUMENTS

| | | | |
|---|---|---|---|
| 2015/0351995 A1* | 12/2015 | Zoss | A61H 1/0244 623/32 |
| 2016/0206498 A1* | 7/2016 | Kazerooni | A61H 1/0244 |
| 2018/0177671 A1* | 6/2018 | Kim | A61B 5/6812 |
| 2019/0091094 A1* | 3/2019 | Romo | A61H 1/0244 |
| 2019/0152047 A1* | 5/2019 | Tosh | B25J 9/0006 |
| 2019/0358807 A1 | 11/2019 | Ohta et al. | |
| 2020/0069441 A1* | 3/2020 | Larose | A61H 1/0281 |

FOREIGN PATENT DOCUMENTS

| | | |
|---|---|---|
| WO | 2018213427 A1 | 11/2018 |
| WO | 2019060791 A1 | 3/2019 |

\* cited by examiner

APPARATUS WEARABLE BY A SUBJECT FOR ASSISTING FORWARD RECLINING MOVEMENTS OF THE TORSO

CROSS REFERENCE TO RELATED APPLICATIONS

This application claims priority from European Patent Application No. 20162846.8 filed on Mar. 12, 2020, the entire disclosure of which is incorporated herein by reference.

TECHNICAL FIELD

The present invention relates to an assistance apparatus wearable by a subject for assisting forward reclining movements of the torso, of the type comprising:
an upper structure for the engagement of the subject's torso and a lower structure for the engagement of the subject's legs,
said upper structure and lower structure being pivotally connected to each other around an axis, and
at least one elastic device operatively interposed between said upper structure and said lower structure.

PRIOR ART

Assistance apparatus wearable by human subjects for receiving assistance in forward reclining movements of the torso have been already known for some time, e.g. by document EP 3046517 B1.

These apparatus are useful when it is necessary to provide a support to subjects who have to spend a long period of time with their torso in the forward reclined position, for example factory workers who perform tasks which involve maintaining a forward reclined position of the torso for many hours in a row. During torso reclining movements, in fact, the muscles and the skeleton of a subject are in a condition of greater tension than when the subject is in an upright position, so that the possibility of using an assistance apparatus allows to relieve the tension even just partially and, consequently, the tiredness perceived by the subject. The relief deriving from the use of an assistance apparatus is even greater in case the subject also has to carry weights or perform tasks in the forward reclined position.

Nevertheless, currently available apparatus have the drawback of being poorly adaptable to physical features of the user, so that there is a risk that they are sometimes felt more as an obstacle to movements rather than as an aid. There is therefore a need of developing alternative solutions without this drawback.

Object of the Invention

An object of the present invention is to implement an apparatus of the type mentioned at the beginning of the present description, which is able to easily and efficiently adapt to the physical features of the human subject wearing it.

A further aim of the present invention is to implement an apparatus of the time mentioned above, which is simple to use and economical to produce.

SUMMARY OF THE INVENTION

In view of achieving one or more of the abovementioned objectives, the invention relates to an assistance apparatus wearable by a subject for assisting forward reclining movements of the torso, comprising:
an upper structure for the engagement of the subject's torso and a lower structure for the engagement of the subject's legs,
the upper structure and the lower structure being pivotally connected to each other around an axis, and
at least one elastic device operatively interposed between the upper structure and the lower structure.

The apparatus is characterized in that it further comprises at least one electric motor operatively arranged in series with the elastic device, between the upper structure and the lower structure, and actionable for dynamically controlling the extent of deformation of the elastic device.

In this way, it is possible to act on the regulation of the motor arranged in series with the elastic device for obtaining any desired variation of the resisting torque felt by the subject when the inclination of the torso changes, which allows to optimally adapt the apparatus both to the physical features of the subject who wears it and, for the same subject, to the type of activity that must be performed.

In an embodiment, the elastic device is an elastic joint comprising a first portion and a second portion rotatably coupled and one or more springs operatively interposed between the first portion and the second portion, wherein the first portion is operatively associated to a shaft driven by the electric motor and the second portion is operatively associated to the upper structure, the electric motor having a body operatively associated to the lower structure.

Preferably, the first portion of the elastic joint has an inner surface comprising a plurality of sectors separated by a plurality of tabs, the plurality of sectors each hosting one or more helical springs, and the second portion of the elastic joint has an inner surface comprising a plurality of teeth, the inner surface of the second portion of the elastic joint facing the inner surface of the first portion of the elastic joint.

In a further embodiment, the elastic device is a spiral spring with axis substantially coincident with the pivot axis and has a first end operatively associated to the upper structure and a second end operatively associated to a shaft driven by the electric motor, having axis substantially coincident with the pivot axis, the electric motor having a body operatively associated to the lower structure.

Preferably, the electric motor is supported with its axis arranged parallel and distanced with respect to the pivot axis between the upper structure and the lower structure and has its motor shaft linked to the driven shaft by means of a reducer belt transmission.

In an embodiment, the electric motor has its axis distanced to the rear with respect to the pivot axis, with reference to the condition of the apparatus worn by a subject.

In this way, the front area with respect to the pivot axis is kept free and thus the electric motor does not constitute an obstacle for the performance of tasks by the subject wearing the apparatus.

In an embodiment, the lower structure comprises two lower lateral semi-structures intended to be associated to the subject's legs respectively and pivotally connected to the upper structure by means of two separate lateral articulation devices, each provided with a respective spring and preferably also with a respective electric motor.

Preferably, the apparatus comprises an electronic controller for controlling the electric motor as a function of signals provided by a sensor of the force exchanged, in the operating condition, between the upper structure and the subject's torso.

In an embodiment, the electronic controller is configured for activating the electric motor only when the force sensor detects the reaching of a predetermined threshold value of the force exchanged, in the operating condition, between the upper structure and the subject's torso.

Preferably, the belt transmission is a toothed belt transmission.

In an embodiment, the upper structure comprises a pair of lateral uprights joint at the top by a support panel for the torso.

Preferably, each of the lower lateral semi-structures is in the form of a substantially L-shaped frame, with a lower vertical portion carrying a support panel for the leg and an upper horizontal portion, protruding to the rear, with reference to the condition worn by a subject, and having an end which carries the body of the respective electric motor.

DETAILED DESCRIPTION OF THE INVENTION

Figure 1:
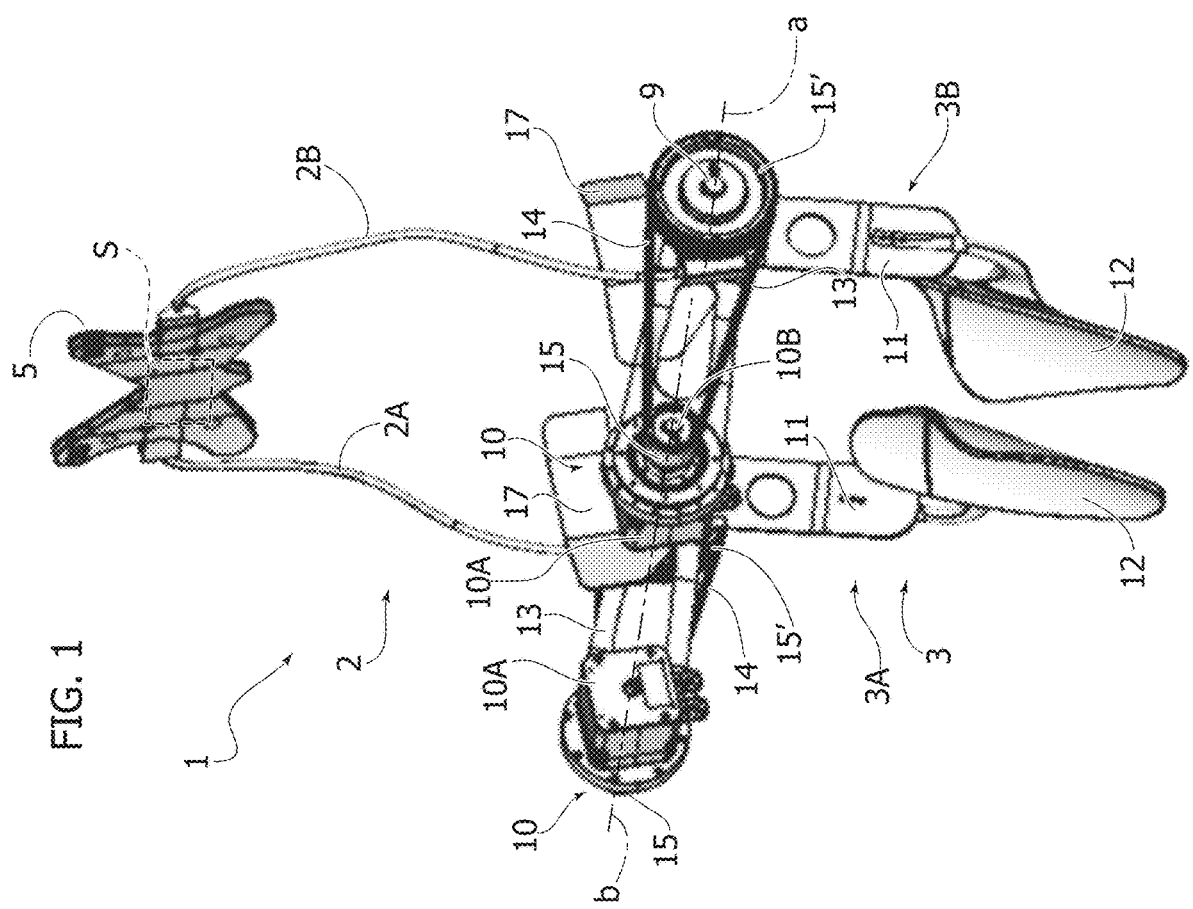
Figure 3:
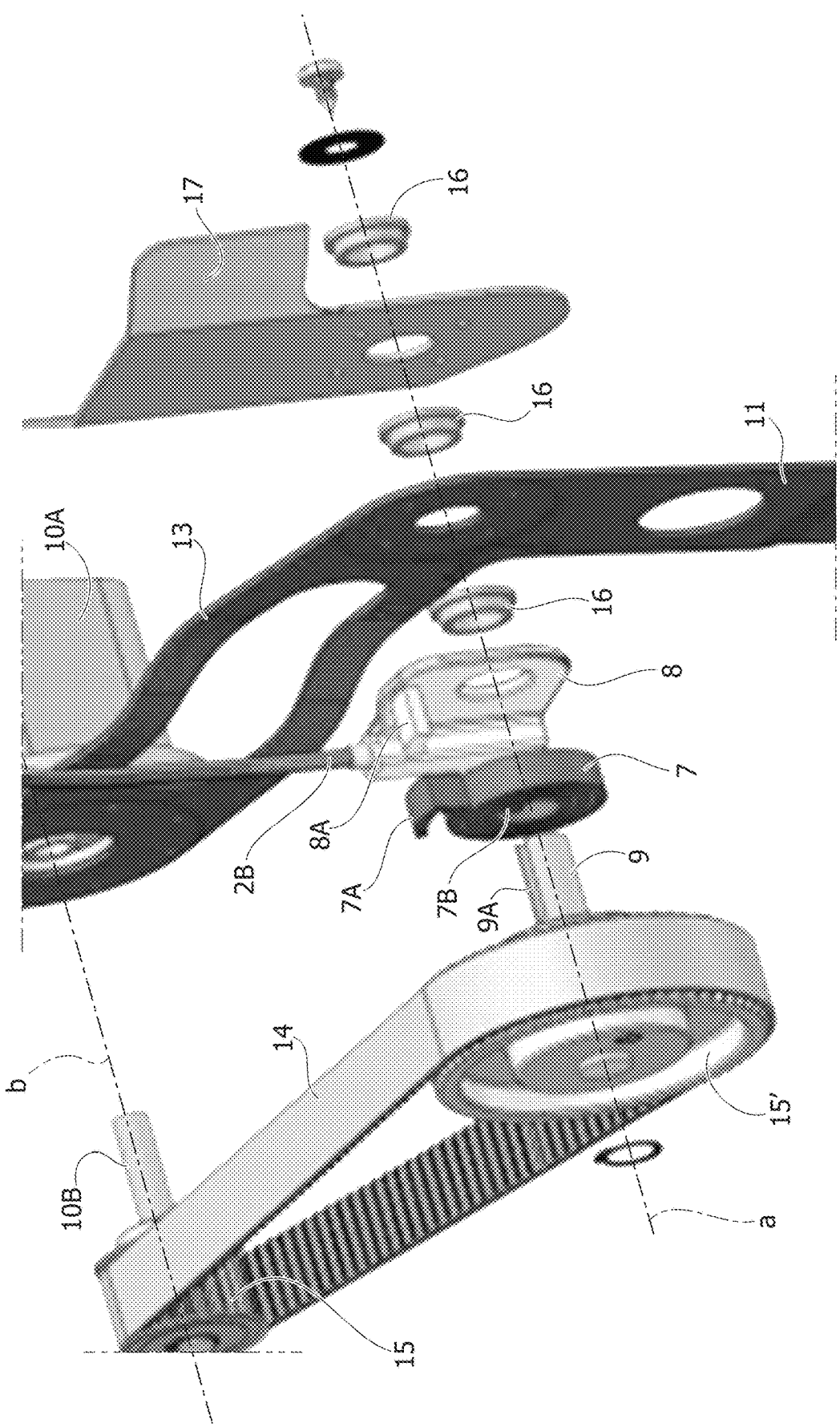
Figure 4:
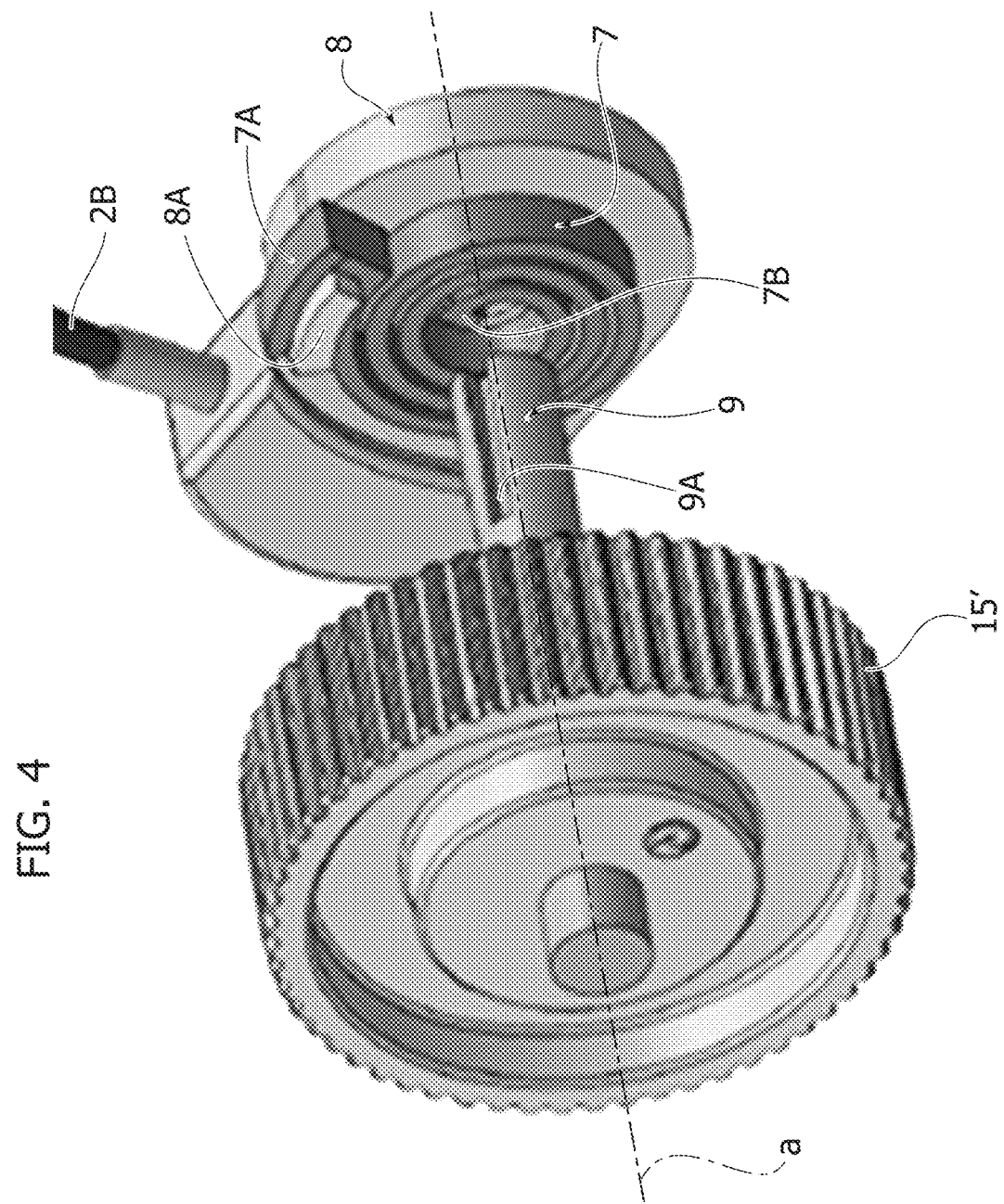
Figure 5:
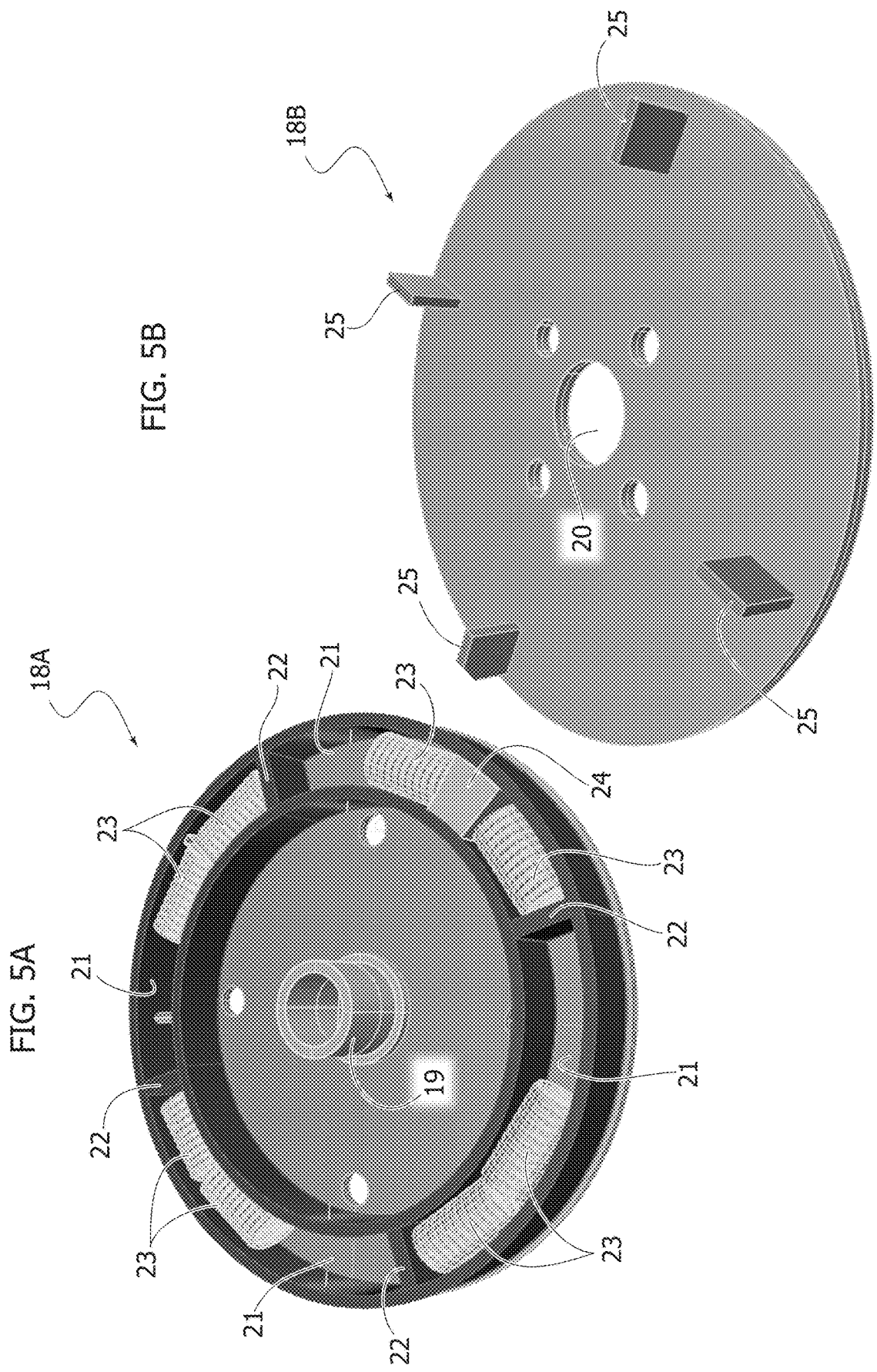
Figure 6:
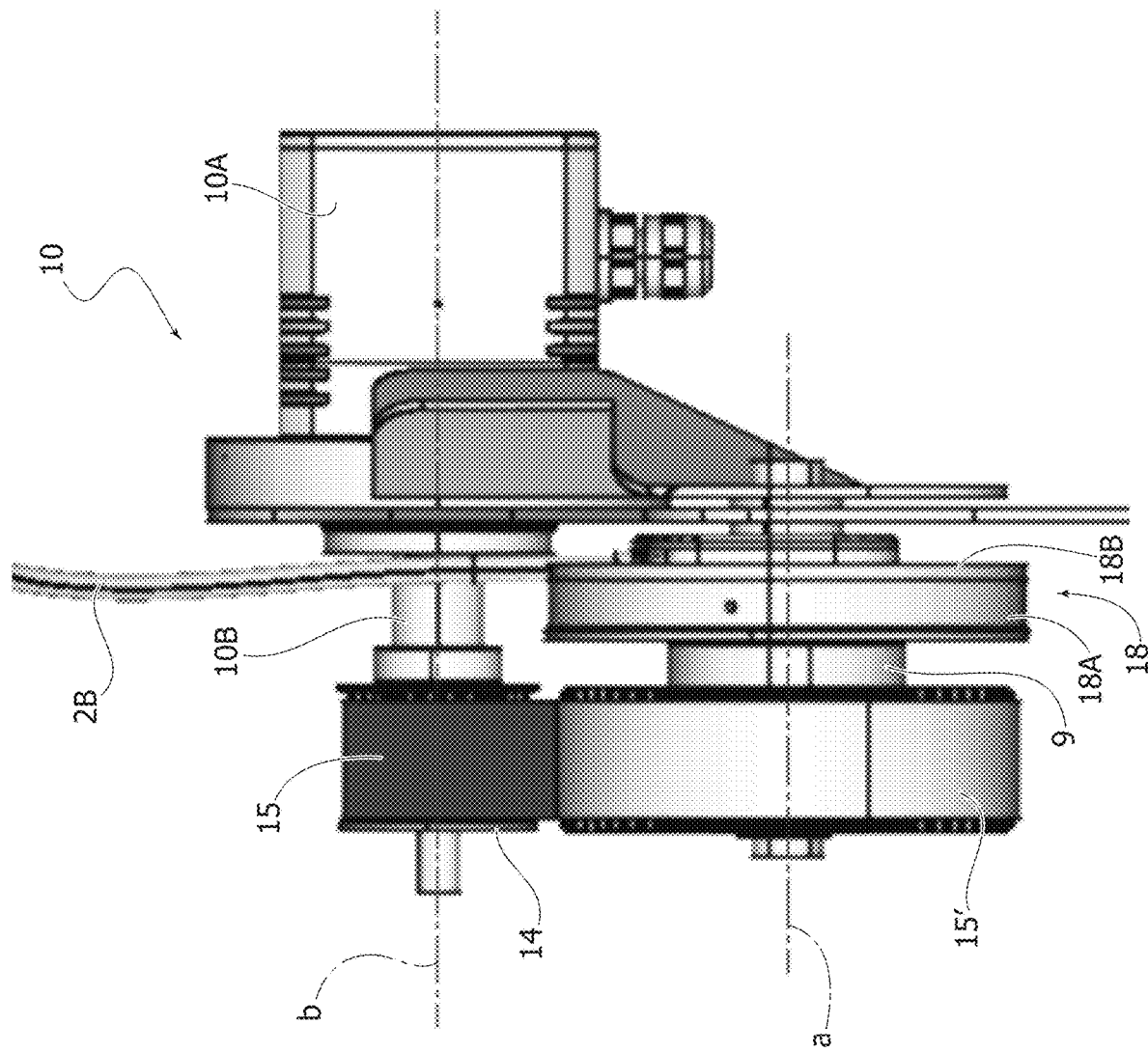
Figure 7:
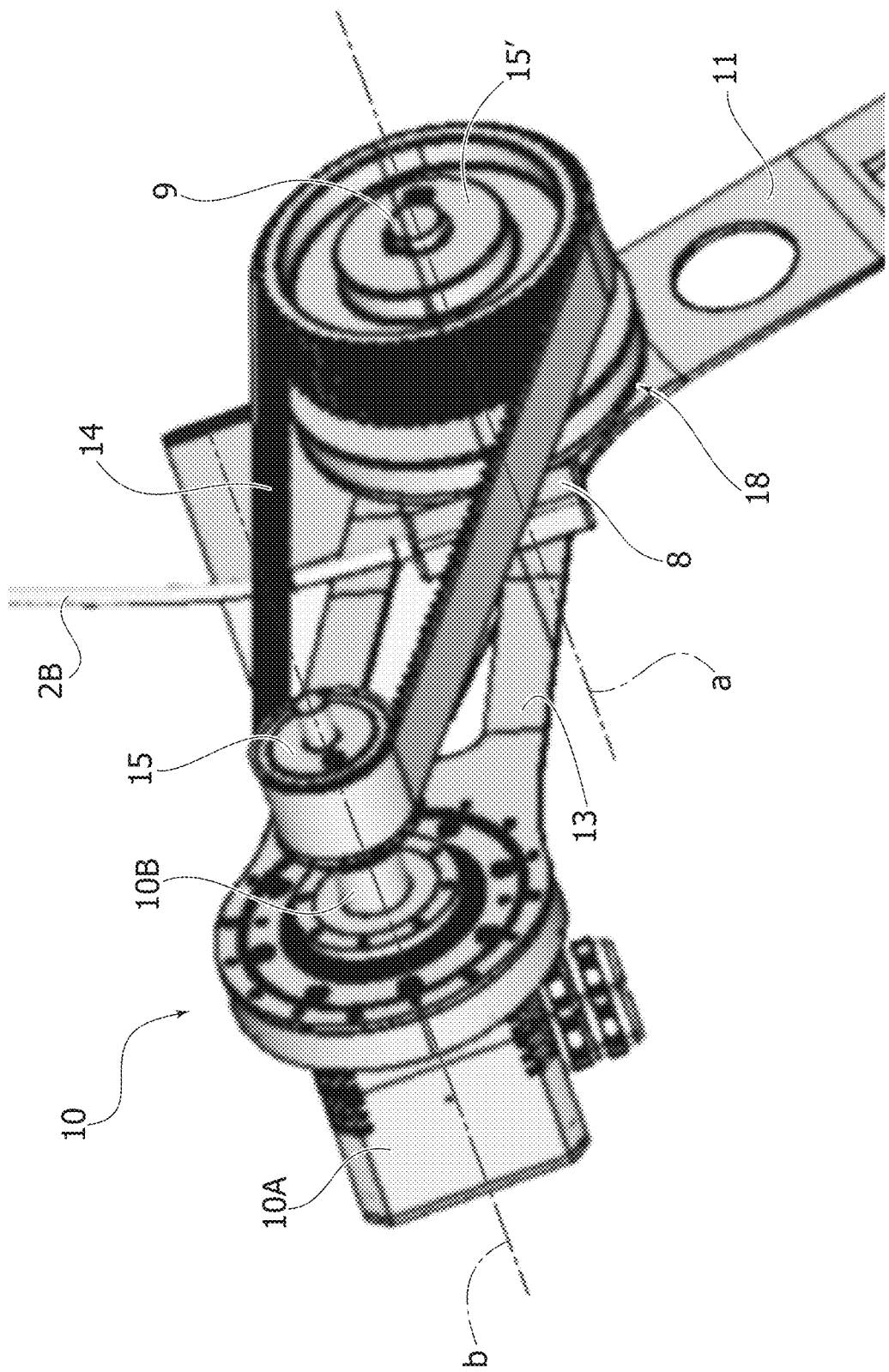
Figure 8:
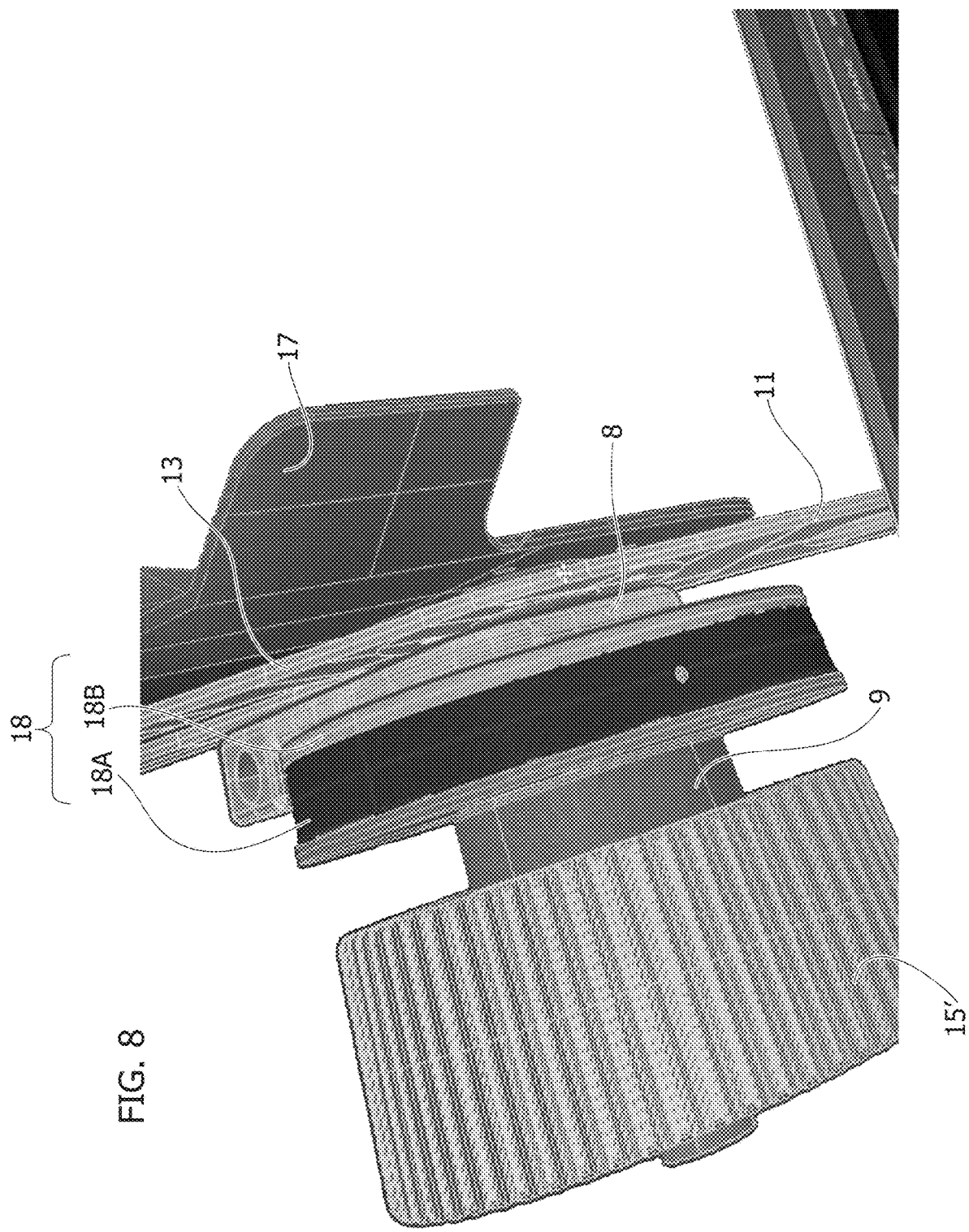
Figure 9A:
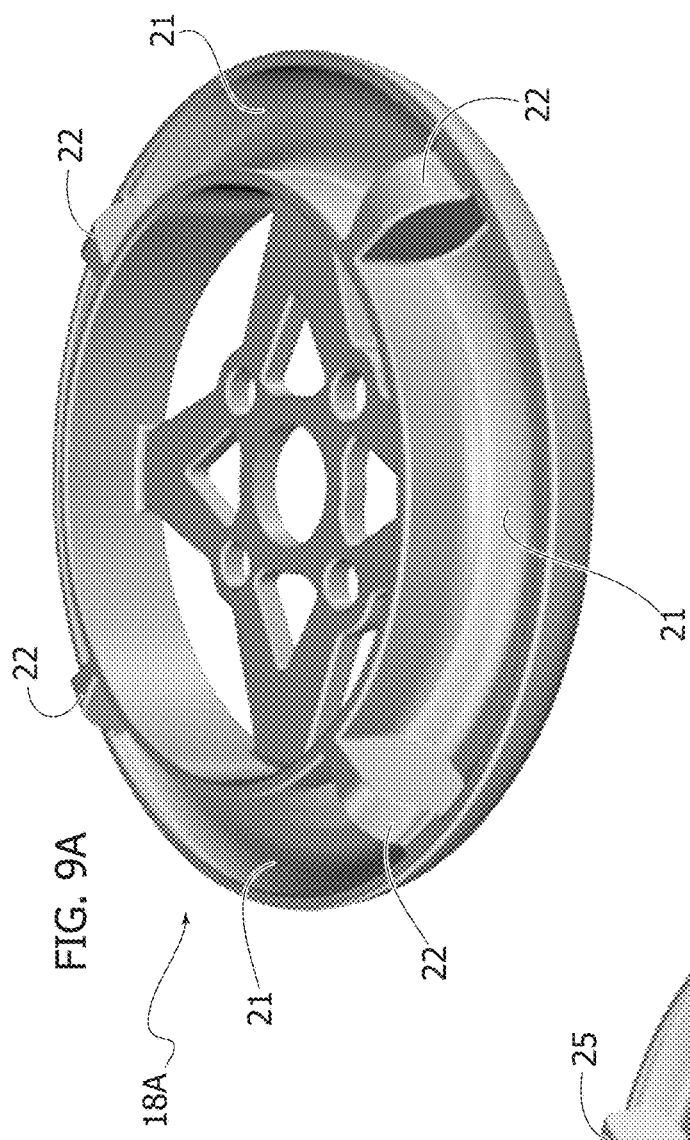
Figure 9B:
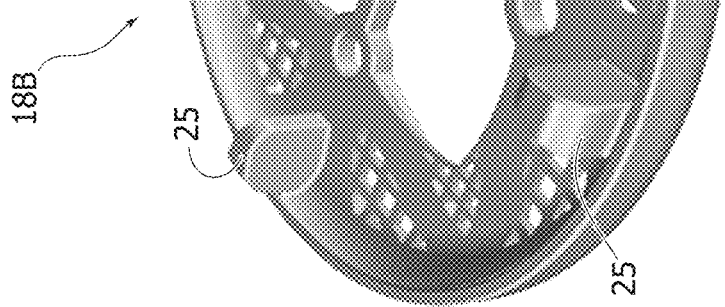
Figure 10:
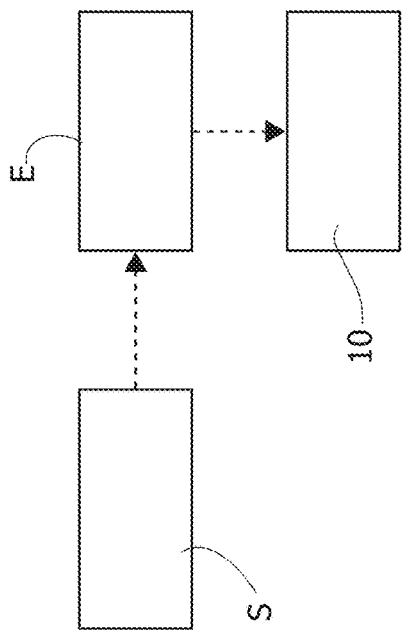

Further characteristics and advantages of the invention will become apparent from the description that follows with reference to the attached drawings, provided purely by way of non-limiting example, wherein:

FIG. 1 is a perspective view of the apparatus subject of the present invention, according to a preferred embodiment, FIG. 2 is a lateral view of the apparatus of FIG. 1, FIG. 3 is an exploded perspective view of one of the two articulation devices provided in the embodiment of FIGS. 1, 2, with the respective electric motor (partially visible) associated to it, in a solution wherein the elastic device comprised in the apparatus subject of the present invention is a spiral spring, FIG. 4 is a perspective view of the portion of connection between the shaft driven by the electric motor and the upper structure of the apparatus of FIGS. 1, 2, at one of the two articulation devices, in a solution wherein the elastic device comprised in the apparatus subject of the present invention is a spiral spring, FIGS. 5A and 5B are two perspective views of the first portion and of the second portion of an elastic joint respectively, with reference to an embodiment wherein said joint is the elastic device of the apparatus according to the invention, FIG. 6 is a front view of the portion of connection between the electric motor, the shaft driven by the electric motor, the elastic joint and the upper structure of the apparatus, FIG. 7 is a perspective view of the portion of connection between the shaft driven by the electric motor and the elastic joint, FIG. 8 is a perspective view of the elastic joint in the mounted condition, FIGS. 9A and 9B are perspective views of the first portion and of the second portion of an elastic joint implemented by additive manufacturing techniques respectively, and FIG. 10 is a block diagram exemplifying the method of control of the electric motor of the apparatus of FIGS. 1, 2.

In FIGS. 1 and 2, numeral 1 indicates in its entirety an assistance apparatus wearable by a subject for an assistance in torso forward reclining movements.

It is understood that the apparatus 1 may be worn both by a male and a female subject.

The apparatus 1 comprises an upper structure 2, provided for the engagement of the subject's torso, and a lower structure 3, provided for the engagement of the subject's legs. The upper structure 2 and the lower structure 3 are pivotally connected to each other around a pivot axis, referenced a in the figures.

As can be seen particularly in FIG. 1, in the preferred embodiment the upper structure 2 comprises a pair of lateral uprights 2A and 2B joint at the top by a panel 5 provided for supporting the torso of the subject wearing the apparatus 1.

It is to be understood that the panel 5 can be of another shape than the one shown in the figures. In particular, the panel 5 can be of any shape that guarantees an adequate freedom of movement of the shoulders and the flex-extension of the neck of the subject wearing the apparatus 1. In the preferred embodiment shown in the figures, the panel 5 is of a substantially butterfly-like shape. This shape is preferred since it has the following advantages:

- it allows to maintain an adequately free area around the subject's joints;
- it allows to avoid bone prominences, processes and tendons of the subject, thus avoiding the risk of onset of stress or injury;
- it allows to avoid areas with superficial vessels or nerves of the subject, so as to limit the risk of injury;
- it allows to avoid heavily sprayed areas such as the subject's armpit and groin, so as to avoid pain or uncomfortable situations;
- it guarantees low pressure values and a high distribution area.

In the example shown (which is non-limiting) the panel 5 is made of a composite material in which the matrix is a polymer and the reinforcement is in carbon fiber.

As can be seen in particular in FIGS. 1 and 2, in the embodiment shown the panel 5 comprises a sensor S of the force exchanged, in the operating condition, between the panel 5 and the torso of the subject wearing the apparatus 1.

In the embodiment shown the sensor S is coated with the coating material of the panel 5, so that it is not visible and is shown dashed. However, this characteristic is not to be understood in a limiting sense, since it is possible that the sensor S is not coated by the coating material of the panel 5 and that it is thus visible. Moreover, even if a single sensor S is represented in the embodiment shown in the figures, it is possible that more than one sensor S is comprised in the panel 5, with the aim of detecting at several points the value of force exchanged, in the operating condition, between the panel 5 and subject's torso.

Again with reference to FIG. 1, in the embodiment shown the lower structure 3 of the apparatus 1 comprises two lower lateral semi-structures 3A and 3B, intended to be associated to each subject's leg respectively. In this embodiment, the two lower lateral semi-structures 3A and 3B are pivotally connected to the upper structure 2 by means of two respective separate lateral articulation devices. The following description refers to each of these articulation devices.

As can be seen in particular in FIGS. 3-9B, each of the two articulation devices includes an elastic device (7; 18) which is operatively interposed between the upper structure 2 and the lower structure 3, in order to recall the apparatus 1 to a configuration corresponding to the user's upright posture.

In the embodiment shown in FIGS. 3 and 4, the elastic device (7; 18) is a spring 7 consisting of a flat tape wrapped in a spiral form, and is substantially concentric with respect to the axis a of articulation between the upper structure 2 and the lower structure 3 of the apparatus 1. Preferably, the spring 7 is made of metallic material. In the preferred embodiment, the spring 7 is made of a steel named 60Si2MnA.

As can be seen in particular in FIG. 4, the spring 7 has a first end 7A operatively associated to the upper structure 2. Preferably, the association between the spring 7 and the upper structure 2 is implemented by means of a support plate 8, rotatably mounted with respect to the lower structure 3, and to which the lower end of the respective lateral upright 2B is connected. The plate 8 has a protrusion 8A capable of engaging the end 7A of the spring 7.

In the embodiment shown in FIGS. 3 and 4, the spring 7 further has a second end 7B operatively associated to a shaft 9 rotatably supported around an axis substantially coincident with the pivot axis a between the upper structure 2 and the lower structure 3. As can be seen in particular in FIG. 4, in the embodiment shown the shaft 9 has a cavity 9A of suitable shape and size for engaging the end 7B of the spring 7.

As can be seen in the embodiment shown in FIGS. 5A-9B, the elastic device (7; 18) operatively interposed between the upper structure 2 and the lower structure 3 is not necessarily a spring 7, but can be, for instance, an elastic joint 18 too.

With reference in particular to FIGS. 5A-5B, the elastic joint 18 comprises a first portion 18A and a second portion 18B which are rotatably coupled to each other. In the embodiment shown, the rotatable coupling between the two portions 18A and 18B is achieved by inserting a cylindrical hub 19, extending from a central part of the first portion 18A, into a corresponding hole 20 of suitable shape and size, formed in a corresponding part of the second portion 18B.

As can be seen in FIG. 5A, the first portion 18A of the elastic joint 18 has an inner surface comprising a plurality of sectors 21, separated by a plurality of tabs 22. In the embodiment shown, the inner surface of the first portion 18A of the elastic joint 18 comprises four sectors 21 separated by four tabs 22, but this characteristic is not to be understood in a limiting sense, since in other embodiments which are not shown the first portion 18A of the elastic joint 18 comprises an higher number or a lower number of sectors 21 separated by a corresponding number of tabs 22. More generally, the elastic joint forming part of this solution could be of any other type known.

A plurality of helical springs 23 is hosted within sectors 21. In the embodiment shown, each sector 21 hosts two helical springs 23, so that a total of eight helical springs 23 is present. However, this characteristic is not to be understood in a limiting sense, since in other embodiments which are not shown, each sector 21 can host a single helical spring 23 or each sector 21 can host a number of helical springs 23 higher than two. It is also possible that a transmission element consisting of a prismatic body 24, e.g. made of rubber, is placed between two helical springs 23 comprised within the same sector 21 to ensure the correct alignment of the springs in series. In the embodiment shown, the helical springs 23 are hosted within the sectors 21 so as to leave a portion of space free from helical springs 23 in each sector 21.

As can be seen in particular in FIG. 5B, the second portion 18B of the elastic joint 18 has an inner surface from which teeth 25 protrude. In the embodiment shown, the inner surface of the second portion 18B comprises four teeth 25, but this characteristic is not to be understood in a limiting sense, since in other embodiments not shown the inner surface of the second portion 18B comprises a higher number or a lower number of teeth 25 than shown in FIG. 5B.

When the coupling between the first portion 18A and the second portion 18B of the elastic joint 18 is implemented, the inner surface of the first portion 18A and the inner surface of the second portion 18B face each other. In particular, the plurality of teeth 25 of the second portion 18B is designed to fit into the space portions of the sectors 21 of the first portion 18A which are free of the helical springs 23.

FIGS. 6-8 show the apparatus having the elastic joint mounted.

Again with reference to FIGS. 6-8, the first portion 18A is operatively associated to the shaft 9 supported in a rotatable manner around an axis substantially coincident with the axis a of articulation between the upper structure 2 and the lower structure 3. In particular, in the represented embodiment, the association between the shaft 9 and the first portion 18A of the elastic joint 18 is implemented thanks to the fact that the cylindrical hub 19 extending from the first portion 18A is hollow, and the cavity has suitable shape and size for receiving the shaft 9 inside itself.

On the other hand, the second portion 18B is operatively associated to the upper structure 3. In particular, the second portion 18B is associated to the support plate 8 rotatably mounted with respect to the lower structure 3.

It is to be understood that the elastic joint 18 can be made of any type of metal or synthetic material. Preferably, the elastic joint 18 is made of an aluminum alloy, more preferably AlSi10Mg.

Moreover, it is possible that the first portion 18A and the second portion 18B of the elastic joint 18 are obtained by applying know methods of additive manufacturing, which allows to obtain versions of the elastic joint 18 after topological optimization, for example as shown in FIGS. 9A, 9B.

The shaft 9 of each of the two articulation devices is driven by a respective electric motor 10 (in the example shown here two electric motors 10 are provided, associated to the two articulation devices respectively) and can be rotated by the motor 10 for dynamically controlling the extent of deformation of the elastic device (7; 18).

As can be seen in particular in FIGS. 1, 3, 6 and 7, each electric motor 10 is supported with its axis b parallel and distanced to the rear with respect to the pivot axis a between the upper structure 2 and the lower structure 3, with reference to the condition of the apparatus 1 worn by a subject. However, this characteristic is not to be understood in a limiting sense, since in other embodiments not shown the electric motor 10 is supported with its axis b parallel and distanced to the front with respect to the pivot axis a between the upper structure 2 and the lower structure 3, with reference to the condition of the apparatus 1 worn by a subject.

With particular reference to FIG. 1, each electric motor 10 has a body 10A operatively associated to the respective lower lateral semi-structure 3A, 3B of the lower structure 3, and a motor shaft 10B, which is linked to the driven shaft 9 by means of a reducer belt transmission 14. In the embodiment shown, the reducer belt transmission comprises two toothed pulleys 15, 15' having diameters selected for obtaining a desired reduction ratio and the belt 14 is a toothed belt. Of course, the possibility of adopting a reducer transmission of any other known type, other than a belt transmission, is not excluded.

With particular reference to FIGS. 1 and 2, in the embodiment shown each of the lower lateral semi-structures 3A, 3B is in form of a substantially L-shaped frame, with a lower vertical portion 11 carrying a support panel 12 for the leg, and an upper horizontal portion 13 protruding to the rear, with reference to the condition worn by a subject and having an end which carries the body 10A of the respective electric motor 10.

In the embodiments shown, the two support panels 12 have a substantially C-shaped structure, in which the concavity is directed towards the leg of the subject wearing the apparatus 1. However, this characteristic is not to be understood in a limiting sense, since the support panels 12 can be of any shape suitable for distributing the support force exerted by the apparatus 1 over an area large enough to avoid localized pressures on the leg, which might be uncomfortable for the subject wearing the apparatus 1. Preferably, the support panels 12 are made of a composite material in which the matrix is a polymer and the reinforcement is carbon fiber.

It is to be understood that the pivotal connection between the upper structure 2 and the lower structure 3 can be implemented in any known way. In the embodiment shown in FIG. 3, this connection is implemented by means of bushes 16, made of any material with a low coefficient of friction, provided for supporting the articulation between the upper structure 2 and the lower structure 3, and for the support in rotation of the driven shaft 9. Moreover, in the embodiment shown in FIG. 3 also a plate 17, containing the pelvis of the subject wearing the apparatus 1, is provided and linked to the upper structure 2. The plate 17 is preferably made of metallic material.

As can be seen in the block diagram shown in FIG. 10, in the represented embodiment the apparatus 1 further comprises an electronic controller E for controlling electric motors 10 according to signals provided by the sensor S. It is to be understood that, in embodiments wherein more than one sensor S is comprised in the panel 5, there may be as many electronic controllers E, each provided for receiving a signal by a specific sensor S and for calculating an average value of these signals.

Preferably, the electronic controller E is configured for activating each electric motor 10 only when the force sensor S detects the reaching of a predetermined threshold value of the force exchanged, in the operating condition, between the panel 5 and the torso of the subject wearing the apparatus 1. In the preferred embodiment, the predetermined threshold value of the force exchanged between the panel 5 and the torso of the subject wearing the apparatus 1 corresponds substantially to an angle of inclination of the upper structure 2 with respect to the lower structure 3 equal to about 20°, measured starting from the upright position of the subject. However, this characteristic is not to be understood in a limiting sense, as it is possible that the electronic controller E is configured for activating the motor 10 when a threshold value of force exchanged between the panel 5 and the torso of the subject wearing the apparatus 1 corresponding to a different value of the angle of inclination between the upper structure 2 and the lower structure 3 is reached.

In use of the embodiments represented in FIGS. 1 to 10, a subject wearing the apparatus 1 for receiving assistance in forward reclining movements of the torso exerts a pressure on the panel 5 with his/her own torso when making these movements. The sensor S included in the panel 5 detects the value of the force exchanged between the panel 5 and the subject's torso and sends the detected value to an electronic controller E, which is programmed for recognizing a threshold value of force.

More specifically, when the value of force exchanged between the panel 5 and the torso of the subject is below the threshold value recognized by the electronic controller E, then each electric motor 10 is not active.

In these conditions, in embodiments wherein the elastic device (7; 18) is a spring 7, this spring 7 of each of the two articulation devices experiences a torsion as a result of the rotation of the upper structure 2 with respect to the lower structure 3, determined by the pressure of the subject's torso on the panel 5, and exerts a resisting torque as a function of its torsion, so that the subject feels an assistance effect from the apparatus 1.

Alternatively, in embodiments wherein the elastic device (7; 18) is an elastic joint 18, under the same conditions described above, the rotation of the upper structure 2 with respect to the lower structure 3 results in a rotation of the second portion 18B, mounted on the support plate 8 in which the respective lateral upright 2A, 2B, of the upper structure 2 is inserted, with respect to the first portion 18A of the elastic joint 18. This rotation involves a displacement of the plurality of teeth 25, included in the second portion 18B, within the free spaces, i.e. not occupied by the helical springs 23, of the sectors 21 of the first portion 18A. More specifically, the rotation involves a compression of the helical springs 23 exerted by the plurality of teeth 25, so that the helical springs 23 exert resisting torques as a function of the compression exerted. As a result, the subject experiences an assistance effect from the apparatus 1.

When the threshold value of the force exchanged between the panel 5 and the torso of the subject wearing the apparatus 1 is reached or exceeded, the electronic controller E activates each electric motor 10, which drives its own motor shaft 10B which, by means of a toothed belt reducer transmission 14, drives the respective driven shaft 9, which is linked to the elastic device (7; 18). In particular, by acting on the adjustment of each electric motor 10 by means of the electronic controller E, it is possible to obtain any desired variation of the resisting torque felt by the subject to the variation of the torso inclination, which allows to adapt in an optimal way the apparatus both to the physical features of the subject who must wear it and, for the same subject, to the type of activity that must be carried out.

It is therefore evident from the description above that the apparatus subject of the present invention is characterized by a greater extent of versatility of use and comfort compared to apparatus currently available.

In addition, the apparatus subject of the present invention is of simple and economic implementation and is easy to use for the person intended to wear it.

It is evident that the apparatus subject of the present invention is particularly advantageous for example in an assembly line in a factory, where it is worn by workers who must remain with the torso in a forward reclined position even for several hours in a row and who may have to perform tasks in that position, such as lifting weights. However, the apparatus subject of the present invention may be used in any other context wherein assistance in the forward reclining movements of a subject's torso is required.

Although the example shown provides two separate lateral articulation devices provided with two respective electric motors, it is also possible to provide a single electric motor connected by means of two transmissions to the two articulation devices.

Naturally, without prejudice to the principle of the invention, the details of construction and the embodiments may vary widely with respect to those described and illustrated purely by way of example, without departing from the scope of the present invention, as defined by the attached claims.

What is claimed is:

1. An assistance apparatus wearable by a subject for receiving assistance in forward reclining movements of the torso, comprising:
   an upper structure for the engagement of the subject's torso and a lower structure for the engagement of the subject's legs, said upper structure and lower structure being pivotally connected to each other around a pivot axis, at least one elastic device operatively interposed between said upper structure and said lower structure, said elastic device having a rotation axis coaxial to said pivot axis; and at least one electric motor operatively arranged in series with said at least one elastic device, between said upper structure and said lower structure, and actionable for dynamically controlling the extent of deformation of said at least one elastic device;

wherein said at least one elastic device is an elastic joint comprising a first portion and a second portion rotatably coupled to each other about the rotation axis and one or more springs operatively interposed between the first portion and the second portion, wherein said first portion is operatively associated to a shaft driven by said at least one electric motor and the second portion is operatively associated to said upper structure, said at least one electric motor having a body operatively associated to said lower structure;

said at least one electric motor having an output shaft axis parallel to and spaced from said pivot axis and said motor driving a driven shaft having a driven shaft axis coaxial to said pivot axis; and wherein the first portion of said elastic joint has a first inner surface comprising a plurality of sectors separated by a plurality of tabs projecting from said inner surface, said plurality of sectors each hosting one or more helical springs, and the second portion of said elastic joint has a second inner surface comprising a plurality of teeth projecting therefrom, said second inner surface of the second portion of the elastic joint facing said first inner surface of the first portion of the elastic joint such that the plurality of teeth is received in the plurality of sectors bounded by the first inner surface and the second inner surface.

2. Apparatus according to claim 1, wherein said at least one elastic device is a spiral spring with a device axis coincident with said pivot axis and having a first end operatively associated to said upper structure and a second end operatively associated to a shaft driven by said at least one electric motor, said electric motor having a body operatively associated to said lower structure.

3. Apparatus according to claim 1, wherein said at least one electric motor is supported with a motor axis thereof arranged parallel and distanced with respect to the pivot axis between said upper structure and said lower structure and has its motor shaft connected to said driven shaft by means of a reducer belt transmission.

4. Apparatus according to claim 3, wherein said at least one electric motor has the motor axis thereof distanced to the rear with respect to the pivot axis, with reference to the condition of the apparatus worn by the subject.

5. Apparatus according to claim 1, wherein said lower structure comprises two lower lateral semi-structures intended to be associated respectively to the subject's legs and pivotally connected to the upper structure by means of two separate lateral articulation devices, each provided with a respective elastic device.

6. Apparatus according to claim 5, wherein each of the two separate lateral articulation devices is associated to a respective electric motor.

7. Apparatus according to claim 1, further comprising an electronic controller for controlling said at least one electric motor as a function of signals provided by a sensor of the force exchanged, in the operating condition, between said upper structure and the subject's torso.

8. Apparatus according to claim 7, wherein the electronic controller is configured for activating said at least one electric motor only when said force sensor detects the reaching of a predetermined threshold value of the force exchanged, in the operating condition, between said upper structure and the torso of the subject.

9. Apparatus according to claim 3, wherein said reducer belt transmission is a toothed belt drive.

10. Apparatus according to claim 1, wherein the upper structure comprises a pair of lateral uprights joint at the top by a support panel for the torso.

11. Apparatus according to claim 6, wherein each of said lower lateral semi-structures is in the form of a L-shaped frame, with a lower vertical portion which carries a support panel for the respective leg and an upper horizontal portion, protruding to the rear, with reference to the condition worn by the subject, and having an end which carries the body of the respective electric motor.

\* \* \* \* \*